United States Patent [19]

Shibue et al.

[11] Patent Number: 5,240,863
[45] Date of Patent: Aug. 31, 1993

[54] METHOD OF MEASURING IMMUNOREACTANT USING ELECTROCHEMILUMINESCENCE

[75] Inventors: Akira Shibue, Koganei; Masaru Tanaka, Chiba; Shinji Kamiya, Koganei, all of Japan

[73] Assignee: TDK Corporation, Tokyo, Japan

[21] Appl. No.: 836,740

[22] Filed: Feb. 19, 1992

[30] Foreign Application Priority Data

Feb. 19, 1991 [JP] Japan ............................. 3-046054
Jul. 23, 1991 [JP] Japan ............................. 3-206336

[51] Int. Cl.$^5$ ............... G01N 33/553; G01N 33/543
[52] U.S. Cl. ............................. 436/526; 436/518; 436/524; 436/525; 436/527; 436/531; 436/532; 436/533; 436/534
[58] Field of Search ............... 435/968; 422/52; 436/523, 524, 525, 526, 527, 534, 546, 518, 531, 532, 533, 534

[56] References Cited

U.S. PATENT DOCUMENTS 4,041,146 8/1977 Giaever.
4,104,029 8/1978 Maier, Jr.
4,280,815 7/1981 Oberhardt et al.

FOREIGN PATENT DOCUMENTS 0087564 9/1983 European Pat. Off.
63-218846 9/1988 Japan.
3-107746 5/1991 Japan.
WO79/00882 11/1979 PCT Int'l Appl.
9005301 5/1990 World Int. Prop. O.

OTHER PUBLICATIONS

Biochemical and Biophysical Research Communications, vol. 128, No. 2, Apr. 30, 1985, pp. 987-992, Y. Ikariyama, et al., "Electrochemical Luminescence-Based Homogeneous Immunoassay".

Primary Examiner—Esther L. Kepplinger
Assistant Examiner—Lora M. Green
Attorney, Agent, or Firm—Oblon, Spivak, McClelland, Maier & Neustadt

[57] ABSTRACT

Detecting an immunoreactant in a liquid sample, by:
mixing the liquid sample with an excess of a complementary immunoreactant capable of specifically binding to the immunoreactant to allow an immunoreaction to take place, in which the complementary immunoreactant is immobilized on insoluble carrier particles and labeled with an electrochemiluminescent substance that emits an electrochemiluminescent light by electrolytic oxidation in the presence of activated oxygen,
applying an electric voltage to a pair of electrodes between which the mixture obtained above is placed, in the presence of activated oxygen to allow electrochemiluminescence to take place;
measuring the emission of the electrochemiluminescent light; and
correlating the presence of the immunoreactant with the amount of measured electrochemiluminescent light, is a highly accurate method, because the rate of change of the emission of luminescent light as a function of immunoreactant concentration in the sample is high.

8 Claims, 2 Drawing Sheets

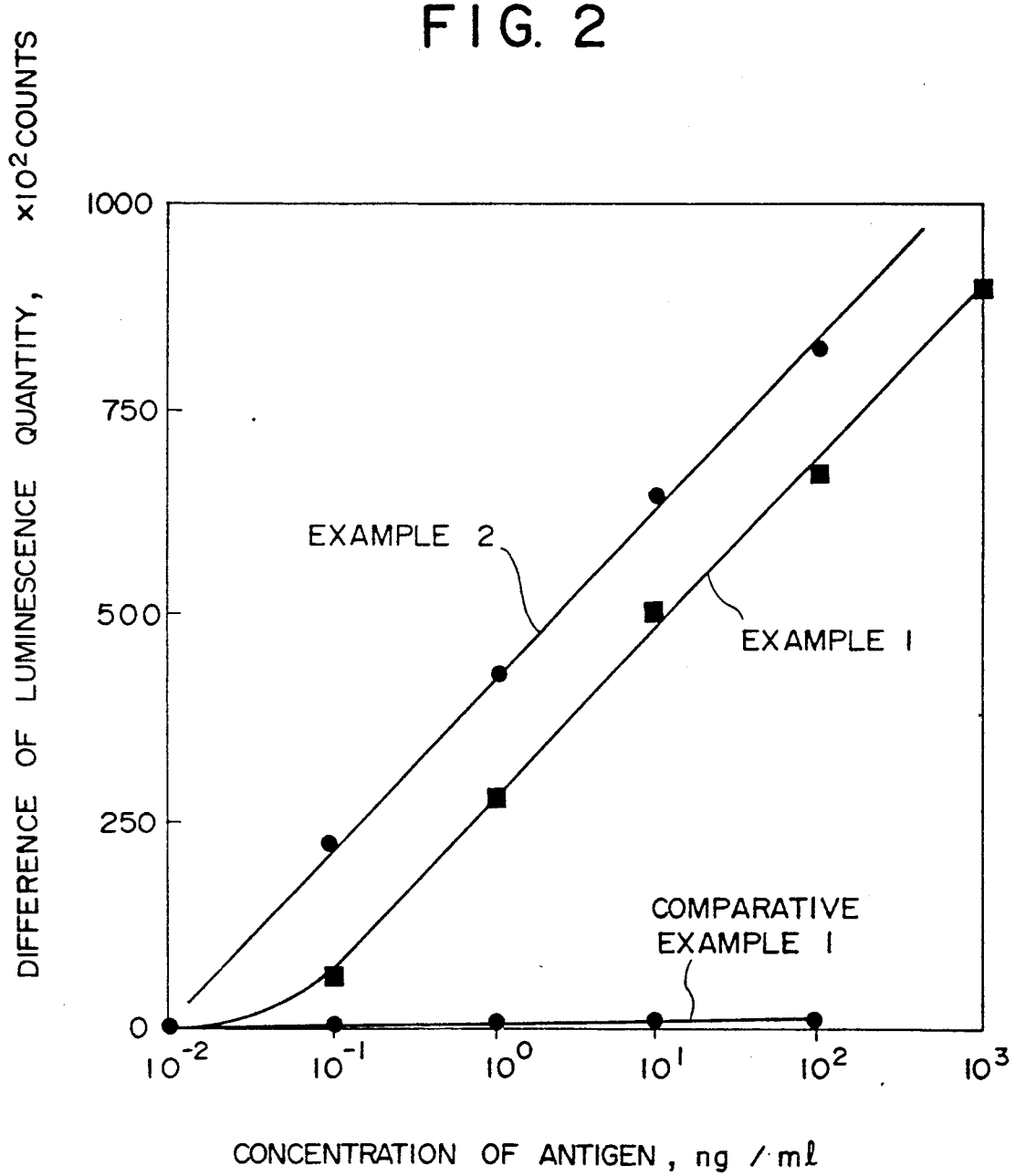

METHOD OF MEASURING IMMUNOREACTANT USING ELECTROCHEMILUMINESCENCE

BACKGROUND OF THE INVENTION

1. Field of the Invention

The present invention relates to a method of measuring an immunoreactant using electrochemiluminescence.

2. Description of the Prior Art

Heretofore, it is known for measurement of an immunoreactant such as antigen or antibody in a liquid sample, to allow the immnoreactant to react with a complementary immnoreactant (antibody or antigen) which has been previously labeled with an electrochemiluminescent substance such as luminol or pyrene. The antigen-antibody reaction occurring between the two immnoreactants suppresses the electrochemiluminescence of the electrochemiluminescent substance labeled on the reacted complementary immunoreactant. Thus, it is possible to measure the concentration of the immunoreactant in the liquid sample by measuring reduction in emission of the electrochemiluminescent light (Y. Ikariyama et al., Biochem. Biophys. Res. Commun., 128, 987 (1985)).

However, the above technique has a defect that the rate of change in emission of the luminescent light depending on the change in the concentration of the antibody to be detected is small, and therefore accuracy of the measurement is low.

SUMMARY OF THE INVENTION

Therefore, an object of the present invention is to provide a method of measuring an immunoreactant such as antigen or antibody, capable of detecting the immunoreactant with good sensitivity or determining the immnoreactant with good accuracy, because the rate of change in emission of electrochemiluminescent light depending on the change in the concentration of the immunoreactant is high.

That is, to attain the above object, the present invention provides a method of measuring an immunoreactant in a liquid sample, comprising the steps of:

mixing the liquid sample with an excess of a complementary immnoreactant capable of specifically binding to said immunoreactant to allow an immunoreaction to take place, said complementary immunoreactant having been immobilized on insoluble carrier particles and labeled with an electrochemiluminescent substance that emits an electrochemiluminescent light by electrolytic oxidation in the presence of an activated oxygen, applying an electric voltage to a pair of electrodes between which the mixture obtained above is placed, in the presence of an activated oxygen to allow electrochemiluminescence to take place, and measuring the emission of the electrochemiluminescent light.

According to the present method, since the rate of change of the emission of luminescent light due to the presence or absence of an immunoreactant to be detected is high, the detection can be carried out with high sensitivity. Further, since the change rate of emission of electrochemiluminescent light depending on the concentration of an immunoreactant is high and therefore the measurement error is very small, an immunoreactant can be determined quantitatively with high accuracy.

The present method can be applied to measurement of any substances that may become antigens and their antibodies.

BRIEF DESCRIPTION OF DRAWINGS

FIG. 2 shows the differences of the emission of electrochemiluminescent light depending on the concentration of an antigen in liquid samples, measured in Example 1, Comparative Example 1, and Example 2 described below.

DETAILED DESCRIPTION OF PREFERRED EMBODIMENTS

Insoluble Carrier Particles

Figure 1:
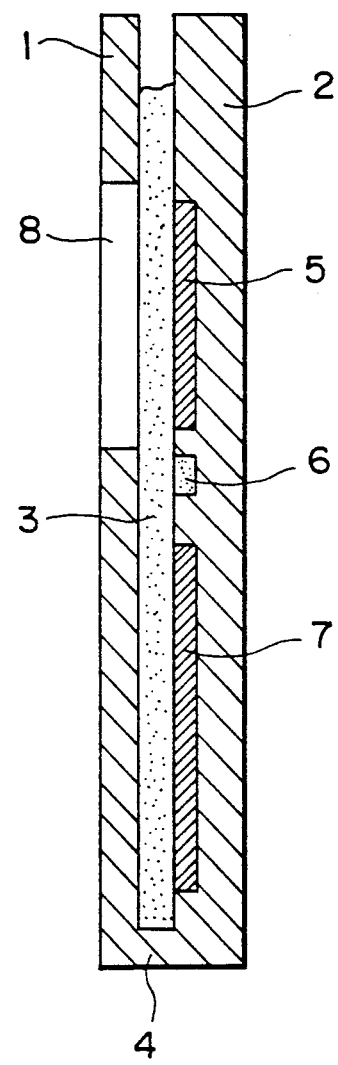
FIG. 1 shows an example of a cell for measuring electrochemiluminescence.

As to insoluble carrier particles used in the present invention, there is no particular restriction if the particles are solid particles that are stable and insoluble in an aqueous medium, and any carrier particles known as carrier for antigens or antibodies conventionally used in antigen-antibody reactions can be used without any particular restriction. Preferable carrier particles include, for example, organic polymer finely divided particles such as organic polymer latexes obtained by emulsion polymerization, e.g., finely divided particles of a polystyrene, a styrene/butadiene copolymer, a styrene/methacrylic acid copolymer, a polyglycidyl methacrylate, and an acrolein/ethylene glycol dimethacrylate copolymer; inorganic oxide finely divided particles such as finely divided particles of silica, silica-alumina, and alumina; $Fe_3O_4$, $\gamma\text{-}Fe_3O_4$, $Co\text{-}\gamma\text{-}Fe_2O_3$, $(NiCuZn)O\text{-}Fe_2O_3$, $(CuZn)O\text{-}Fe_2O_3$, $(Mn\text{-}Zn)O\text{-}Fe_2O_3$, $(NiZn)O\text{-}Fe_2O_3$, $SrO\text{-}6Fe_2O_3$, $BaO\text{-}6Fe_2O_3$, $Fe_3O_4$ coated with $SiO_2$ (having a particle diameter of about 150–500 Å) [see "Enzyme Microb. Technol.," vol. 2, pp 2–10 (1980)], composite finely divided particles of various polymer materials, e.g., nylons, polycrylamides, and proteins, with ferrite, and magnetic metal finely divided particles. Generally, the particle diameter of these insoluble carrier particles is preferably 1.0 μm or below. Among the above-mentioned particles, the magnetic finely divided particles diameter preferably has a particle diameter of 50 to 500 Å where they are used singly. The other finely divided particles including composite particles of the magnetic finely devided particles with a polymer material preferably have a particle diameter of about 0.05 to 0.4 μm.

Among the finely divided particles of the abovementioned materials and having the above particle diameter, particularly preferable finely divided particles include $Fe_3O_4$ particles coated with $SiO_2$ and having a particle diameter of 150–500 Å and $\gamma\text{-}Fe_3O_4$ particles having a particle diameter of 200 to 300 Å. Such preferable magnetic finely divided particles further include finely divided particles having a particle diameter of 150–500 Å, comprising as a major component iron and containing Ni and Co which are produced by a heat plasma method in a liquid phase in which carbon coexists.

The complementary immunoreactant immobilized on the insoluble carrier particles that can be used in the present invention can be produced by immobilizing a prescribed complementary immunoreactant to the above insoluble carrier particles. A variety of immobilizing techniques are known, and any of the methods using physical adsorption and the methods using formation of chemical covalent boding can be used. Generally, physical adsorption is suitable to immobilize a protein highly capable of being physically adsorbed such as antibodies or a protein having a high molecular weight, while formation of chemical covalent bonding is suitable to immobilize hormones and haptens which are low in capability of being physically adsorbed. The immobilizing method may be selected suitably depending, for example, on the properties of the complementary immunoreactant to be immobilized. Where inorganic oxide particles or magnetic finely divided particles out of the above-mentioned finely divided particles are used as the insoluble carrier particles, it is recommended to introduce functional groups onto the insoluble carrier particles as conventionally performed, for example, by treating with a silane coupling agent or coating with protein A produced by *staphylococcus aureus*.

Generally, as a dispersing medium a buffer is used, and insoluble carrier particles and a complementary immunoreactant is mixed therein, if desired, after a dispersing agent is added. Although there is no particular restriction on the dispersing agent used therein, in view of the stability of the insoluble carrier particles during their storage and the reproducibility of the reaction at the time of agglutination, a buffer such as a glycine/sodium hydroxide buffer, a Tris-HCl buffer, an ammonium chloride/ammonia buffer, and a phosphate buffer can be suitably used.

The antibody or antigen used as the complementary immunoreactant to be immobilized to the insoluble carrier particles needs to have complementary relationship with a particular immunoreactant, i.e., antigen or antibody to be measured. Examples of such an antigen or antibody to be measured or used as the measuring means are shown below, but the present invention is not restricted to them at all.

Antigens: IgG, IgA, IgM, IgE, albumins, HCG, AFP, cardiolipin antigen, blood group substances, concanavalin A, DNT, prostaglandins, CRP, HBs, human growth hormones, steroid hormones, CEA, IgD, etc.

Antibodies: anti-albumin antibodies, anti-HCG antibodies, anti-IgG antibodies, anti-IgA antibodies, anti-IgM antibodies, anti-IgE antibodies, anti-IgD antibodies, anti-AFP antibodies, anti-DNT antibodies, anti-prostagladin antibodies, anti-human clotting factor antibodies, anti-CRP antibodies, anti-HBs antibodies, anti-human growth hormone antibodies, anti-steroid hormone antibodies, serums containing them, anti-steroid hormone antibodies, and monoclonal antibodies.

Electrochemiluminescent Substances

As the electrochemiluminescent substance to be used as a marker, any of those known to exhibit electrochemiluminescence by electrolytic oxidation in the presence of an activated oxygen, can be used. Examples include luminol, pyrene, luciferin and their electrochemiluminescent derivatives such as isoluminol, N-aminohexyl-N-ethylluminol, N-aminobutyl-N-ethyl isoluminol (ABEI) and activated ester derivatives of ABEI. Among these, preferred is luminol. The electrochemiluminescent substance as a marker may be affixed to the insoluble carrier particles or on the immobilized complementary immunoreactant or on both of them.

The activated oxygen herein means atomic oxygen, oxygen in the form of hydrogen peroxide, and other oxygen and oxide in an activated state that generate by electrochemical reaction. Such an activated oxygen may be made present or to generate in the mixture when the voltage is applied by adding previously hydrogen peroxide to the mixture or electrochmically reducing oxygen molecules which are dissolved in the aqueous solution or are previously added. The hydrogen peroxide is added preferably in an amount of 0.01 to 10 mmol/liter, more preferably 0.3 to 3 mmol/liter.

Measurement

According to the present method, to detect or determine an immunoreactant in a liquid sample, first the immunoreaction or antigen-antibody reaction between the immunoreactant and an excess of an immobilized complementary immunoreactant is allowed to take place, followed by effecting electrochemiluminescence, and emission of the electrochemiluminescent light is measured.

For example, in an embodiment of the present method, it further comprises the step of comparing the measured emission electrochemiluminescent light with the emission of the light measured for a control sample not containing the immunoreactant to be detected, to detect the presence or absence of the immunoreactant.

In another embodiment of the present method, it further comprises the step of comparing the measured emission of light with a previously made calibration curve showing the relationship between the concentration of the immunoreactant and the emission of the luminescent light.

The method of the present invention is suitable in the cases where the concentration of the immunoreactant to be detected is in the range of $10^{-11}$ to $10^{-6}$ g/ml. The immunoreactant immobilized on an insoluble career particles are normally mixed with the liquid sample so that the concentration thereof may be in the range of 0.01 to 1 mg/l, preferable about 0.1 mg/l, and at that time the complementary immunoreactant on the carrier particles is normally present in an amount of 10 to 1,000 µg, preferably 100 to 400 µg per gram of the carrier particles.

If the liquid sample contains an immunoreactant to be detected, the labeled and immobilized complementary immunoreactant reacts with the immunoreactant. The quantity of the reacted labeled and immobilized complementary immunoreactant depends on the quantity of the immunoreactant present in the liquid sample. The reacted electrochemiluminescently labeled and immobilized complementary immunoreactant is difficult to participate in electrochemiluminescence which will be caused by subsequent application of an electric voltage. The suppression of the electrochemiluminescence is far more intense as compared with the case where the complementary immunoreactant is not immobilized on carrier particles. Therefore, a slight change in the quantity of the labeled and immobilized complementary immunoreactant that has undergone the antigen-antibody reaction results in a great change in emission quantity of electrochemifluorescent light. That is, the change rate of emission of electrochemiluminescent light depending on the change in concentration of an immunoreactant to be detected in a liquid sample, is large.

The electric voltage applied to said pair of electrodes between which the reaction mixture is provided, is controlled such that the electric potential of an electrode serving as the anode or the working electrode is not less than the electric potential at which the electrochemiluminescent substance exhibits electrochemiluminescence and not higher than an electric voltage at which a gaseous oxygen generates. To control the electric potential of the anode or the working electrode suitably, a reference electrode is preferably used.

The labeled and immobilized complementary immunoreactant is generally added in the form of an aqueous suspension to a liquid sample. There is no particular restriction on the method of the addition. A given amount of the suspension containing the insoluble carrier particles in a given concentration may be added to a given amount of a liquid sample, or alternatively the latter may be added to the former.

If magnetic finely divided particles are used as the insoluble carrier particles, for example, it is possible that the suspension disclosed in Japanese Preexamination Patent Application (kokai) No. 63-90766(1988), that is, a suspension wherein magnetic finely divided particles having a particle diameter of 50 to 500 Å to which a complementary immunoreactant has been immobilized are dispersed in an isotonic aqueous salt solution containing 0.1 wt. % or more of a surface active agent with the amount of the isotonic aqueous solution being 5 ml or more per mg of the magnetic finely divided particles, is previously prepared and is added to a liquid sample. Such a suspension is convenient because it is highly stable and good in storage stability. As the isotonic aqueous salt solution, for example, a 0.9% NaCl solution or a 0.025M aqueous sucrose solution can be used. The surface active agent to be added to the isotonic aqueous salt solution includes surface active agents having a group —COOH or —COO$^-$, such as Tween 80. It is required that the concentration of the surface active agent in the isotonic aqueous salt solution is 0.1 wt. % or over, preferably 0.1 to 1.0 wt. %.

In the method of the present invention, to disperse the insoluble carrier particles into a liquid sample, for example, ultrasonic waves can be used. The dispersion treatment of the sample liquid into the suspension allows the immunoreactant present in the liquid sample to bind to the complementary immunoreactant immobilized on the carrier particles to thereby produce a complex of the immunoreactant/complementary immunoreactant/carrier particles. For this treatment, various methods can be used, for example, a method of forming a complex of immunoreactant/complementary immunoreactant/magnetic finely divided particles by applying an alternating field as described in Japanese Pre-examination Patent Application (kokai) No. 02-281142(1990) and methods using stirring can be used, and there is no particular restriction. Presumably, once said complex is thus formed, when an electric voltage is applied the electrochemiluminescent substance incorporated in the complex is difficult to participate in the electrochemiluminescence due to the steric hindrance by the insoluble carrier particles in comparison with the case where the complementary immunoreactant is not immobilized to carrier particles.

The method of the present invention can be carried out using a variety of cells based on the two electrode system or the three electrode system for measurement of electrochemiluminescence.

Utility

The method of the present invention can be used for all the purposes for which conventional immunoassays have been utilized. In addition, since the method is suitable for microdetermination, it can be applied to measurement of substances that cannot measured by conventional immunoassays. For example, the method is useful for diagnosis of malignant tumors by measuring serum components, e.g., a marker substance for a tumor such as α-fetoprotein. The method is expected to be applied to measurement of hormones and steroids with a small molecular weight and drags in blood.

EXAMPLES

Example 1

(1) After 2 mg of finely divided magnetic particles having a particle diameter of 120 Å was treated with -aminopropylethoxysilane and then with glutaraldehyde, 2 mg of anti-human IgG antibody was added thereto, thereby immobilizing the antibody to the magnetic finely divided particles through covalent bonding. Then the anti-human IgG-immobilized magnetic finely divided particles were reacted with 1 mg of diazotized luminol to label the anti-human IgG-immobilized magnetic finely divided particles with luminol.

(2) The anti-human IgG-immobilized magnetic finely divided particles labeled with luminol was dispersed in a PBS (phosphate buffered saline) containing 0.6 wt. % of Tween 80 and having a pH of 7.4 so that the concentration of the magnetic finely divided particles might be 0.2 mg/ml. The thus obtained dispersion was mixed with each of a control solution containing no human IgG (0 ng/ml) and 6 sample solutions whose human IgG concentrations were known, i.e., $1 \times 10^{-2}$ ng/ml, $1 \times 10^{-1}$ ng/ml, $1 \times 10^0$ ng/ml, $1 \times 10^1$ ng/ml, $1 \times 10^2$ ng/ml and $1 \times 10^3$ ng/ml, respectively, with the volume ratio being 1:1, and the antigen-antibody reaction was thereby allowed to proceed. The reaction was effected at room temperature for 10 min with an alternating magnetic field having a magnetic flux density of 200 gauss and a pulse width of 0.5 sec being applied.

(3) The cell for measurement of electrochemiluminescence schematically shown in FIG. 1 was used. In the cell, two plates constituting the wall 1 and the wall 2 are disposed 1 mm apart opposite to each other so as to form a inner space 3 with a volume of 500 μm, and the both sides and the bottom 4 are sealed. On the inner surface of the wall 2, a Pt-working electrode 5 (thickness: 0.3 mm; area: 0.32 cm$^2$) and a Pt-counter electrode 6 (thickness: 0.3 mm; area: 0.6 cm$^2$) and a reference electrode 6 (Ag/AgCl electrode) are provided. In the area in the wall 1 opposite to the working electrode 5, a transparent window 8 made of polymethacrylate with a thickness of 1 mm is provided. This window has a light transmittance of more than 90% at 425 nm. For the measurement of the quantity of emission of luminescence, the reaction mixture and a PBS containing hydrogen peroxide in an amount of $10^{-3}$ mol per liter were mixed with the volume ratio being 1:1, then after the mixed liquid was allowed to stand for 10 min at room temperature, 500 μl of the liquid was placed in the above cell, an electric voltage was applied to the working electrode for 15 sec using an electric potential generating apparatus so that the electric potential of the working electrode might be +1200 mV with respect to the electrical potential of the Ag/AgCl reference electrode, thereby causing the luminol to emit luminescent light. The emission quantity of luminescence was measured by a photon counting system which uses as an optical detector a photomultiplier disposed outside and close to the window 8.

The differences between the emission quantity measured for the control solution and that measured for the six liquid samples are shown in FIG. 2.

COMPARATIVE EXAMPLE 1

A PBS containing 50 μm/ml of a luminol-labeled anti-human IgG antibody which had been labeled by diazotizing luminol was prepared. 500 μl of this labeled antibody solution was mixed with 500 μl of each of 5 sample solutions having human IgG concentrations of $1\times10^{-2}$ mg/ml, $1\times10^{-1}$ mg/ml, $1\times10^{0}$ mg/ml, $1\times10^{1}$ mg/ml and $1\times10^{2}$ mg/ml, respectively, and each of the mixtures was stirred slowly at room temperature for 3 hours to allow antigen-antibody reaction to take place. Each of the reaction mixtures was mixed with a PBS containing $10^{-3}$ mol of hydrogen peroxide per liter with the volume ratio being 1:1. After the mixture was then allowed to stand for 10 min at room temperature, the measurement of emission of luminescent light was carried out in the same way as in Example 1.

The obtained results are shown in FIG. 2.

EXAMPLE 2

Polystyrene latex particles having an average particle diameter of 0.023 μm were diluted with a Tris-HCl buffer (pH: 7.5) to prepare a suspension having a latex concentration of 1 wt. %. Then, anti-human IgG was diluted with Tris-HCl buffer (pH: 7.5) to prepare a solution having a protein concentration of 2 mg/ml. 1 ml of the anti-human IgG was added to 1 ml of the above latex suspension and they were allowed to react for at 37° C. for 2 hours. Similarly, 1 ml of a luminol solution (having a concentration of 0.1 mmol/1) was added to that solution and the reaction was effected at 37° C. for 2 hours. Further, bovine serum albumin was added so that the final concentration might be 0.05%, then centrifuging was effected, the supernatant was removed, and the sediment was redispersed in Tris-HCl buffer (pH: 7.5) to prepare an anti-human IgG-immobilized latex labeled with luminol which had a latex concentration of 0.08 wt. %.

The same measurement as that in (2) and (3) of Example 1 was carried out, except that the reaction was effected with slow stirring for 10 min without applying an alternation field. The obtained results are shown in FIG. 2.

We claim:

1. A method of detecting the presence or amount of an immunoreactant in a liquid sample, comprising the steps of:
    mixing the liquid sample with an excess of a complementary immunoreactant capable of specifically binding to said immunoreactant to allow an immunoreaction to take place, said complementary immunoreactant having been immobilized on insoluble carrier particles and labeled with an electrochemiluminescent substance that emits an electrochemiluminescent light by electrolytic oxidation in the presence of activated oxygen;
    applying an electric voltage to a pair of electrodes between which the mixture obtained above is placed, in the presence of activated oxygen to allow electrochemiluminescence to take place;
    measuring the emission of the electrochemiluminescent light; and
    correlating the presence or amount of said immunoreactant with an amount of measured electrochemiluminescent light.

2. The method according to claim 1, wherein the labeled and immobilized complementary immunoreactant to be mixed with said liquid sample is in the form of a suspension.

3. The method according to claim 1, wherein said immunoreactant is an antigen and said complementary immunoreactant is an antibody that specifically binds to said antigen.

4. The method according to claim 1, wherein said immunoreactant is an antibody and said complementary immunoreactant is an antigen that specifically binds to said antibody.

5. The method according to claim 1, wherein said insoluble carrier particles are organic polymer finely divided particles, inorganic oxide finely divided particles, composite finely divided particles of a polymer material and ferrite, or magnetic metal finely divided particles.

6. The method according to claim 1, wherein said insoluble carrier particles have a particle diameter of 1.0 μm or less.

7. The method according to claim 1, wherein said electrochemiluminescent substance is luminol, pyrene, luciferin, or an electrochemiluminescent derivative thereof.

8. The method according to claim 1, wherein the potential of the electrode that serves as a working electrode is controlled using a reference electrode.

* * * * *